United States Patent
Park et al.

(10) Patent No.: US 8,937,165 B2
(45) Date of Patent: Jan. 20, 2015

(54) PROTEINIC MARKER FOR EARLY DIAGNOSIS OF LIVER CANCER

(75) Inventors: Jin Young Park, Seoul (KR); Seok Joo Hong, Daejeon (KR); Jongmin Kim, Seoul (KR); Youngtack Shim, Seoul (KR)

(73) Assignees: CBSBioscience Co., Ltd., Daejeon (KP); Youngtack Shim, Seoul (KP)

( * ) Notice: Subject to any disclaimer, the term of this patent is extended or adjusted under 35 U.S.C. 154(b) by 411 days.

(21) Appl. No.: 12/922,557

(22) PCT Filed: Mar. 12, 2009

(86) PCT No.: PCT/KR2009/001225
§ 371 (c)(1),
(2), (4) Date: Oct. 13, 2010

(87) PCT Pub. No.: WO2009/113814
PCT Pub. Date: Sep. 17, 2009

(65) Prior Publication Data
US 2011/0033873 A1 Feb. 10, 2011

(30) Foreign Application Priority Data
Mar. 14, 2008 (KR) .......... 10-2008-0023911

(51) Int. Cl.
*C07K 16/32* (2006.01)

(52) U.S. Cl.
USPC .................................. 530/389.7

(58) Field of Classification Search
None
See application file for complete search history.

(56) References Cited

U.S. PATENT DOCUMENTS

2005/0089895 A1* 4/2005 Cheung et al. ............... 435/6

FOREIGN PATENT DOCUMENTS

| KR | 10-2003-0092378 A | 12/2003 |
|----|-------------------|---------|
| KR | 10-2003-0092462 A | 12/2003 |
| KR | 10-2004-0039597 A | 5/2004 |
| KR | 10-2005-0076876 A | 7/2005 |
| KR | 10-0767878 B1 | 10/2007 |

OTHER PUBLICATIONS

Kuramitsu et al (proteomics 2006, 6:5650-5661).*
Tannapfel et al (J of Pathology, 2003, 201:238-249).*
NCBI: Apolipoprotein A-I sequence (NCBI GI:113992), printed Mar. 2013.*
NCBI: apolipoprotein A-I isoform CRA b sequence (GI:119587681), printed Mar. 2013.*
Hugo Gene Nomenclature Committee "VCL" printed Mar. 2013.*
Hugo Gene Nomenclature Committee "AKR1C4" printed Mar. 2013.*
Hugo Gene Nomenclature Committee "TOR1AIP1" printed Mar. 2013.*
Seow et al (Electrophoresis, 2000, 21:1787-1813).*
Kim et al (Clinical Cancer Research, 2003, 9:5493-5500).*
International Search Report for PCT/KR2009/001225 dated Dec. 17, 2009.
International Preliminary Report on Patentability for PCT/KR2009/001225 dated Sep. 14, 2010.
Yi Feng, et al., "Protein profile of human hepatocarcinoma cell line SMMC-7721: Identification and functional analysis," World Journal of Gastroenterology, May 14, 2007, 13(18).

* cited by examiner

*Primary Examiner* — Laura B Goddard
(74) *Attorney, Agent, or Firm* — Joseph Bach; Ronald I. Eisenstein; Mark J. FitzGerald

(57) ABSTRACT

The present invention relates to proteomic markers for early detection of hepatocellular carcinoma, compositions for detecting changes of these proteomic markers, kits for detection of hepatocellular carcinoma, methods for detecting proteomic markers including these compositions, methods for screening drugs for hepatocellular carcinoma using these proteomic markers, and antibodies specific for these proteomic markers.

2 Claims, 4 Drawing Sheets

PROTEINIC MARKER FOR EARLY DIAGNOSIS OF LIVER CANCER

FIELD OF THE INVENTION

The present invention relates to proteomic markers for early detection of hepatocellular carcinoma, compositions for detecting changes of these proteomic markers, kits for detection of hepatocellular carcinoma, methods for detecting proteomic markers including these compositions, methods for screening drugs for hepatocellular carcinoma using these proteomic markers, and antibodies specific for these proteomic markers.

BACKGROUND OF THE INVENTION

Cancer has an identical meaning with malignant tumor and indicates a state where regulation of cellular growth is damaged due to various causes and thus abnormal cells excessively grow and thus invade surrounding tissues and organs, form masses, and destroy normal tissues. Cancers typically exhibit rapid growth, invasiveness (penetrate into or spread out), and metastasis (moves to the remote place), which eventually leads to a life-threatening condition.

Liver cancer is one of the most lethal cancers worldwide, and the death toll from liver cancer each year exceeds half million people in Asia and Sub-Saharan Africa. Liver cancer is classified into primary liver cancer (hepatocellular carcinoma) that originates from liver cells and metastatic liver cancer that originates from other malignant tissues. More than 90% of the liver cancer is primary liver cancer, and therefore, liver cancer is typically understood as indicating primary liver cancer.

Although the etiological agents of hepatocellular carcinoma are well known to be an acute or a chronic hepatitis with hepatitis B virus and hepatitis C virus infection, the molecular mechanism in vivo of hepatocarcinogenesis has not been clarified.

Previous studies identified that cancers including liver cancer are induced by mutation of proto-oncogenes such as growth factors to oncogenes which leads to overexpression and overactivation of oncogenes, or by mutation of tumor suppressors such as RB and p53 which leads to their loss of function or underexpression. Especially, the relevance of genes such as mutated p53, beta-catenin, axin 1, p21(WAF1/CIP1), and p27Kip, etc to hepatocellular carcinoma has been identified. However, the current view on cancers have changed such that it is now understood that cancers including liver cancer are not caused by a few genes alone, but originated from the complex interactions of many genes related to cell cycle and signal transduction processes. Therefore, rather than focusing on expression levels and functions of a few genes or proteins, a more comprehensive analysis of diverse set of genes and proteins would be required.

Cancer is known to be the most typical refractory disease. Treatments of cancers can be categorized as surgery, cancer chemotherapy, and radiation therapy. Other treatment methods include locoregional therapy, hormone therapy, photodynamic therapy (PDT), laser therapy etc, and more recently immunotherapy and gene therapy is attempted. For a successful treatment of cancer, the early detection of cancer is essential.

More than 90% of early stage cancers can be treated completely with less than 5% recurrence rate. However, cancers, especially liver cancer, do not show any observable symptoms that enables early detection of cancer, thus there is a difficulty in detecting a cancer early by a conventional method.

Several methods are under development for early detection of cancer, one of which is utilizing cancer specific markers that are originated from bodily fluids and tissues that indicates in the presence of cancer. Genes or proteins that are specifically overexpressed or underexpressed in cancer cells can be used as cancer specific markers. The presence of these cancer specific markers in the tissues or bodily fluids from the patients at risk of cancer can be used to diagnose cancer. For example, AFP is known as a liver cancer marker, which is present at very low levels in normal adults (less than 7-10 ng/mL), but at much higher levels in 50-70% of HCC patients. These cancer specific markers can provide possibility of early detection of cancer due to their easy and accurate diagnostic utility, provide clues to the mechanism of carcinogenesis through in-depth study of their functions, and ultimately provide staring points for development of cancer treatment and prevention. Thus, development of cancer specific markers has important meanings for both academic and medical aspects.

Previous research on liver cancer markers include Xu et al. [Xu et al., Cancer Res. 61:3176-3181, 2001] that described analysis of cDNA library from 29 liver cancer tissues and matching surrounding normal tissues and found genes frequently expressed in hepatocellular carcinoma: serum albumin, α1-antitrypsin, inter-alpha-trypsin inhibitor, Apolipoprotein AII, fibrinogen, selenoprotein P, aldolase; Park et al. [Park et al., Int. J. Cancer 62:276-282, 1995] that reported increased expression of transferrin, IGF-II (insulin-likegrowth factor II), IGF-1R (insulin growth factor-1 receptor), and Fas-ligand related to apoptosis in HCC.

Previous patent documents on liver cancer markers are Korean patent No. 552,494 (registered in 2006 Feb. 8) that described liver cancer specific overexpression of K-ALPHA-1 (NM_006082), LDHA (NM_005566), FTL (NM_000146), ANXA2 (NM_004039), RPL4 (NM_000968), ENO1 (NM_001428), RPL9 (NM_000661), GNB2L1 (NM_006098), RPL10 (NM_006013), RPL13A (NM_012423) and liver cancer specific underexpression of AMBP (NM_001633), SERPINC1 (NM_000488), GC (NM_000583), A1BG (NM_130786) genes; Korean patent No. 777088 (registered in 2007 Nov. 9) that described LCN2 (NM_005564), MIDKINE (NM_002391, NM_001012333, NM_001012334), TFPI (NM_006287); Korean patent No. 2007-99312 (2007 Oct. 9) that described HLA-DMA (NM_006120), CD24 (NM_013230), SDFR1 (NM_012428); Korean patent No. 767,878 (registered in 2007 Oct. 10) that described UBD (Hs.44532), PRKAG1 (Hs.3136), CSTB (Hs.695), PSORS1C1 (Hs.507), TUBBS (Hs.110837), Hs.62914, UBPH (Hs.3459), SPARC (Hs.111779), PDHB (Hs.161357), EIF4B (Hs.93379), ABCB10 (Hs.1710), NDFIP2 (Hs.30340), SPAG7 (Hs.90436), RAN (Hs.10842), DDIT4 (Hs.111244), RPS20 (Hs.8102), C9orf9 (Hs.62595), TBC1D14 (Hs.72242), PIP5K2A (Hs.108966), SNX22 (Hs.157607), C9 (Hs.1290), CYP2E1 (Hs.75183), ZFP36L1 (Hs.85155), C6 (Hs.1282), BHMT (Hs.80756), MICAL3 (Hs.165551), DKFZp434C0328 (Hs.24583), GZMB (Hs.1051), PCK1 (Hs.1872), UGT2B7 (Hs.10319), MGC45564 (Hs.132230), UBE4A (Hs.75275), KIAA0316 (Hs.92025), ADH1C (Hs.2523), RPS9 (Hs.139876), SFXN1 (Hs.135742), SLC12A8 (Hs.36793), APOA1 (Hs.93194), BF (Hs.69771), and ACAT1 (Hs.37). However, the liver cancer markers listed in the above patent documents have been identified at the DNA or mRNA level rather than at the proteome level, and none of them used early HCC tissues. The genetic material in cancer cells are typically unstable such that the expression levels of genes unrelated to cancer are often affected, and thus, the applicability or clinical accuracy of liver cancer markers identified at the DNA or mRNA level using fully-developed cancer tissues are questionable. Therefore, there is still a need for clinically applicable and accurate liver cancer markers.

Proteome is the whole gamut of proteins that can be synthesized from genome, which is a dynamic entity that reflects changes within specific physiological and pathological states of cells or tissues. Proteomics is the area of research that encompasses the methods and techniques to characterize proteome, focusing on characteristics of proteins in relation with gene expression, post-translational modification, protein complex formation to comprehensively understand changes and network formation within cells and progression of diseases. Thus, Proteome represents the physiological and pathological states within cells and tissues, and thus it is one of the best approaches to find diagnostic markers of diseases. Further, if the expression of certain genes induces carcinogenesis, the protein coded by such genes could be identified and used as target proteins for drug development. The development of diagnostic and therapeutic drugs are under way using genomics approach because of its high sensitivity and easy amplification of genetic materials. However, the changes at the DNA or mRNA level may not lead to changes at the protein level, undermining the usefulness of markers developed at the DNA or mRNA level. Furthermore, in case of genetic materials that cannot be easily acquired for bodily fluids, proteomics analysis is the most practical approach. The body fluids such as plasma, serum, urine, cerebrospinal fluid, amniotic fluid, and secreting fluid are used for non-invasive approaches towards diagnosis of the disease and many researchers rely on proteomics methods to develop specific protein markers.

SUMMARY OF THE INVENTION

The present invention aims to provide proteomic markers for early detection of hepatocellular carcinoma, compositions for detecting changes of these proteomic markers, kits for detection of hepatocellular carcinoma, methods for detecting proteomic markers including these compositions, methods for screening drugs for hepatocellular carcinoma using these proteomic markers, and antibodies specific for these proteomic markers.

BRIEF DESCRIPTION OF THE DRAWINGS

FIG. 2. 2D Gel images (pI 3-5.6 NL) of Edmondson grade I hepatocellular carcinoma tissues (n=2), Edmondson grade II hepatocellular carcinoma tissues (n=4), and surrounding noncancerous tissues (n=5).

FIG. 4. 2D Gel images (pI 6.2-7.5 L) of Edmondson grade I hepatocellular carcinoma tissues (n=2), Edmondson grade II hepatocellular carcinoma tissues (n=4), and surrounding noncancerous tissues (n=5).

DETAILED DESCRIPTION

Figure 1:
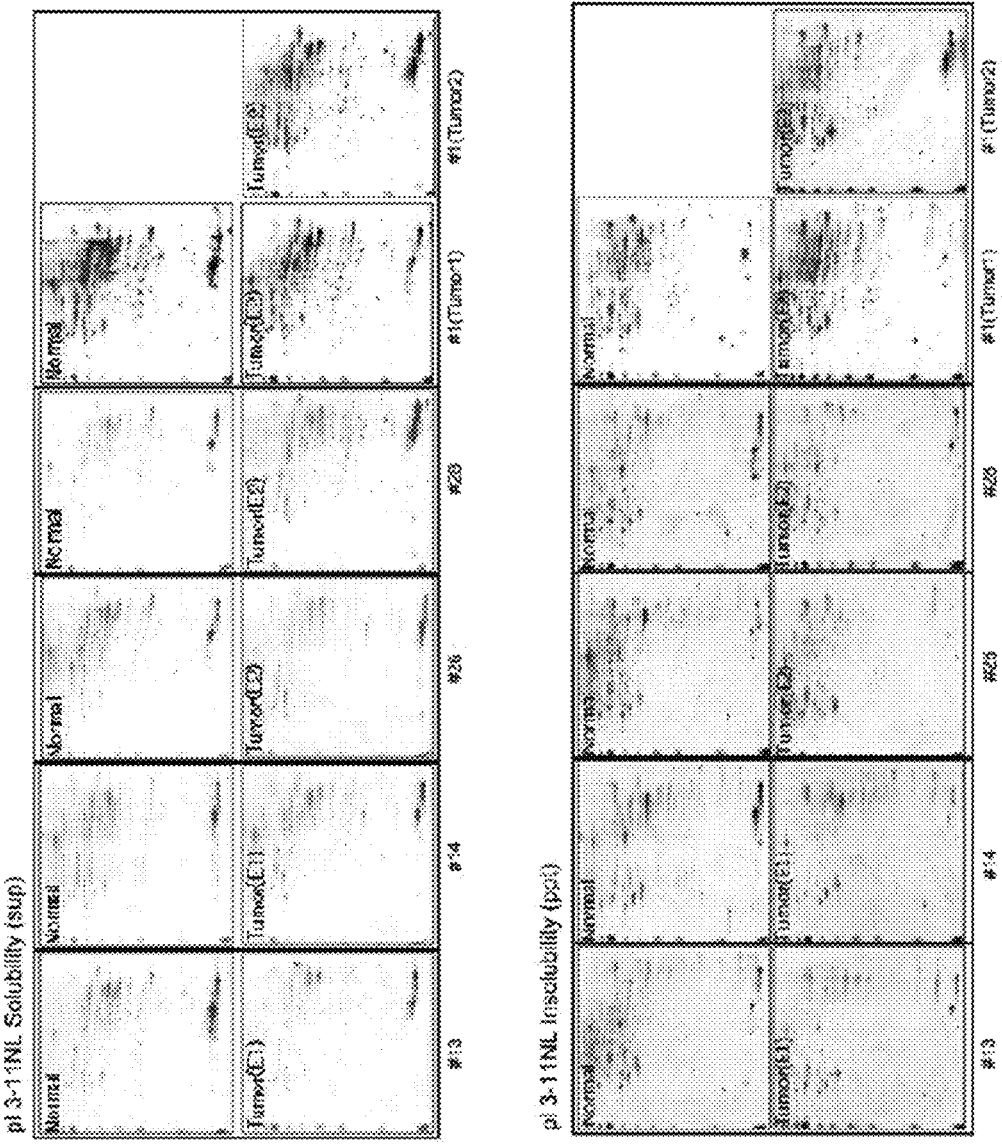
FIG. 1. 2D Gel images (pI 3-11 NL) of Edmondson grade I hepatocellular carcinoma tissues (n=2), Edmondson grade II hepatocellular carcinoma tissues (n=4), and surrounding noncancerous tissues (n=5).

The inventors developed proteomic markers for early detection of liver cancer by identifying specifically overexpressed and underexpressed proteins through comparison and analysis of the proteomes of normal liver tissues and early hepatocellular carcinoma tissues.

The first aspect of the present invention relates to proteomic markers for early detection of liver cancer comprising one or more of the following polypeptides:

AA1XP52_HUMAN (catecholamine-regulated protein 40; NCBI GI:94450030);

ARSA1_HUMAN (arsA arsenite transporter, ATP-binding, homolog 1; NCBI GI:50428938);

MAAI_HUMAN (glutathione transferase zeta 1; NCBI GI:3510757);

UGDH_HUMAN (UDP-glucose dehydrogenase; NCBI GI:4507813);

NDUS3_HUMAN (NADH dehydrogenase (ubiquinone) Fe—S protein 3, 30 kDa (NADH-coenzyme Q reductase); NCBI GI:4758788);

FTHFD_HUMAN (formyltetrahydrofolate dehydrogenase isoform a variant; NCBI GI:3560541);

ATP5H_HUMAN (ATP synthase, H+ transporting, mitochondrial F0 complex, subunit d isoform a; NCBI GI:5453559);

ERLN2_HUMAN (ER lipid raft associated 2 isoform 1; NCBI GI:6005721);

SNP29_HUMAN (synaptosomal-associated protein 29; NCBI GI:4759154);

AIFM1_HUMAN (programmed cell death 8 isoform 2; NCBI GI:22202629);

LDHA_HUMAN (lactate dehydrogenase A variant; NCBI GI:62897717);

ADA_HUMAN (adenosine deaminase; NCBI GI:47078295);

CO3_HUMAN (Chain B, Human Complement Component C3; NCBI GI:78101268);

LMNA_HUMAN (lamin A/C isoform 2; NCBI GI:5031875);

APOA1_HUMAN (apolipoprotein A-I, isoform CRA_b; NCBI GI:119587681);

FRIH_HUMAN (FTH1 protein; NCBI GI:76779199);

ANXA1_HUMAN (Chain A, Crystal Structure Of Human Annexin I At 2.5 Angstroms Resolution; NCBI GI:157829895);

ARLY_HUMAN (argininosuccinate lyase; NCBI GI:18033920);

APT_HUMAN (adenine phosphoribosyltransferase isoform a; NCBI GI:4502171);

HSP71_HUMAN (heat shock 70 kDa protein 1B; NCBI GI:147744565);

HS90B_HUMAN (90 kDa heat shock protein; NCBI GI:306891);

ADH4_HUMAN (Alcohol dehydrogenase 4 (Alcohol dehydrogenase class II pi chain); NCBI GI:83286923);

GSTA2_HUMAN (glutathione S-transferase A2 subunit; NCBI GI:257476);

VILI_HUMAN (villin 1; NCBI GI:6005944);

ODB2_HUMAN (branched chain acyltransferase precursor; NCBI GI:179354);

PYC_HUMAN (pyruvate carboxylase precursor; NCBI GI:106049292);

KU70_HUMAN (ATP-dependent DNA helicase II, 70 kDa subunit; NCBI GI:4503841);

KU86_HUMAN (ATP-dependent DNA helicase II; NCBI GI:10863945);

TCTP_HUMAN (tumor protein, translationally-controlled 1; NCBI GI:4507669);

PLSL_HUMAN (L-plastin; NCBI GI:4504965);

ACPH_HUMAN (N-acylaminoacyl-peptide hydrolase; NCBI GI:23510451);
GLNA_HUMAN (GLUL protein; NCBI GI:22749655);
AK1C4_HUMAN (Aldo-keto reductase family 1 member C4 (Chlordecone reductase) (CDR); NCBI GI:1705823);
TCPA_HUMAN (T-complex protein 1 isoform a; NCBI GI:57863257);
VINC_HUMAN (vinculin; NCBI GI:4507877);
TYPH_HUMAN (endothelial cell growth factor 1 (platelet-derived); NCBI GI:4503445);
IREB1_HUMAN (aconitase 1; NCBI GI:8659555);
ODBB_HUMAN (chain B, human branched-chain alpha-keto acid dehydrogenase; NCBI GI:7546385);
TGM2_HUMAN (transglutaminase 2 isoform a; NCBI GI:39777597);
CPT2_HUMAN (carnitine palmitoyltransferase II; NCBI GI:4503023);
EF1B_HUMAN (eukaryotic translation elongation factor 1 beta 2; NCBI GI:4503477);
MOES_HUMAN (moesin; NCBI GI:4505257);
EF1G_HUMAN (eukaryotic translation elongation factor 1 gamma, isoform CRA_d; NCBI GI:119594432);
AOFB_HUMAN (monoamine oxidase B; NCBI GI:38202207);
1433T_HUMAN (tyrosine 3/tryptophan 5-monooxygenase activation protein, theta polypeptide; NCBI GI:5803227);
PSB9_HUMAN (proteasome beta 9 subunit isoform 2 proprotein; NCBI GI:23110932);
TKT_HUMAN (transketolase; NCBI GI:4507521);
AL4A1_HUMAN (aldehyde dehydrogenase 4A1 precursor; NCBI GI:25777734);
ERP29_HUMAN (endoplasmic reticulum protein 29 isoform 1 precursor; NCBI GI:5803013);
2AAA_HUMAN (Chain A, Structure Of A Complex Between The A Subunit Of Protein Phosphatase 2a And The Small T Antigen Of Sv40; NCBI GI:149243188);
AL1B1_HUMAN (aldehyde dehydrogenase 1B1 precursor; NCBI GI:25777730);
QCR1_HUMAN (ubiquinol-cytochrome c reductase core protein I; NCBI GI:46593007);
HNRH1_HUMAN (heterogeneous nuclear ribonucleoprotein H1; NCBI GI:5031753);
1433B_HUMAN (tyrosine 3-monooxygenase/tryptophan 5-monooxygenase activation protein, beta polypeptide; NCBI GI:4507949);
PRDX2_HUMAN (peroxiredoxin 2 isoform2; NCBI GI:32189392);
ACSL1_HUMAN (acyl-CoA synthetase long-chain family member 1; NCBI GI:40807491);
PHB_HUMAN (prohibitin; NCBI GI:4505773);
CBS_HUMAN (cystathionine-beta-synthase; NCBI GI:4557415);
MYH9_HUMAN (Nonmuscle myosin heavy chain A; NCBI GI:189030);
ODO2_HUMAN (dihydrolipoamide succinyltransferase; NCBI GI:643589);
PEX19_HUMAN (peroxisomal biogenesis factor 19; NCBI GI:4506339);
LPPRC_HUMAN (leucine-rich PPR motif-containing protein; NCBI GI:31621305);
CAZA2_HUMAN (capping protein alpha; NCBI GI:433308);
UCRI_HUMAN (ubiquinol-cytochrome c reductase, Rieske iron-sulfur polypeptide 1; NCBI GI:5174743);
TCPE_HUMAN (chaperonin containing TCP1, subunit 5 (epsilon); NCBI GI:24307939);
AL9A1_HUMAN (4-trimethylaminobutyraldehyde dehydrogenase (TMABADH) (Aldehyde dehydrogenase family 9 member A1) (Aldehyde dehydrogenase E3 isozyme) (Gamma-aminobutyraldehyde dehydrogenase) (R-aminobutyraldehyde dehydrogenase); NCBI GI:62511242);
HINT1_HUMAN (histidine triad nucleotide binding protein 1; NCBI GI:4885413);
ST1A1_HUMAN (phenol sulfotransferase; NCBI GI:847763);
SSRD_HUMAN (signal sequence receptor, delta; NCBI GI:5454090);
GDIR_HUMAN (Chain A, Structure Of Rho Guanine Nucleotide Dissociation Inhibitor; NCBI GI:2624719);
KAD2_HUMAN (adenylate kinase 2 isoform b; NCBI GI:7524346);
SNAA_HUMAN (N-ethylmaleimide-sensitive factor attachment protein, alpha; NCBI GI:47933379);
TERA_HUMAN (Valosin-containing protein; NCBI GI:6005942);
1433E_HUMAN (tyrosine 3/tryptophan 5-monooxygenase activation protein, epsilon polypeptide; NCBI GI:5803225);
1433Z_HUMAN (tyrosine 3/tryptophan 5-monooxygenase activation protein, zeta polypeptide; NCBI GI:4507953);
SKP1_HUMAN (S-phase kinase-associated protein 1 isoform b; NCBI GI:25777713);
ACTG_HUMAN (ACTB protein; NCBI GI:15277503);
HBB_HUMAN (beta globin; NCBI GI:4504349);
TCPB_HUMAN (CCT2; NCBI GI:48146259);
SET_HUMAN (SET translocation (myeloid leukemia-associated); NCBI GI:145843637);
MMSA_HUMAN (aldehyde dehydrogenase 6A1 precursor; NCBI GI:11095441);
BDH_HUMAN (3-hydroxybutyrate dehydrogenase precursor; NCBI GI:17738292);
LGUL_HUMAN (glyoxalase I; NCBI GI:118402586);
ST2A1_HUMAN (sulfotransferase family, cytosolic, 2A dehydroepiandrosterone-preferring, member 1; NCBI GI:29540545);
C1QBP_HUMAN (tat-associated protein; NCBI GI:1096067);
PRDX4_HUMAN (thioredoxin peroxidase; NCBI GI:5453549);
FCL_HUMAN (tissue specific transplantation antigen P35B; NCBI GI:4507709);
DPYS_HUMAN (dihydropyrimidinase; NCBI GI:4503375);
GANAB_HUMAN (Glucosidase II; NCBI GI:2274968);
MVP_HUMAN (major vault protein; NCBI GI:19913410);
UGPA_HUMAN (UTP-glucose-1-phosphate uridylyltransferase; NCBI GI:2136353);
IMMT_HUMAN (motor protein; NCBI GI:516766);
GLE1_HUMAN (GLE1 RNA export mediator homolog isoform 2; NCBI GI:4557627);
Q56G89_HUMAN (serum albumin; NCBI GI:62113341);
TOIP1_HUMAN (torsin A interacting protein 1, isoform CRA_b; NCBI GI:119611474);
Q5U0A0_HUMAN (proteasome (prosome, macropain) subunit, alpha type, 5; NCBI GI:54696300);
F108B_HUMAN (family with sequence similarity 108, member B1 isoform 2; NCBI GI:71051602);
HIBCH_HUMAN (3-hydroxyisobutyryl-coenzyme A hydrolase; NCBI GI:3320120);
DCXR_HUMAN (dicarbonyl/L-xylulose reductase; NCBI GI:7705925);

PTOV1_HUMAN (prostate tumor overexpressed gene 1, isoform CRA_b; NCBI GI:7920398);
GLCTK_HUMAN (CG9886-like; NCBI GI:31543063);
CS010_HUMAN (R33729_1; NCBI GI:3355455);
FAH2A_HUMAN (CGI-105 protein; NCBI GI:4929679);
ABHEB_HUMAN (abhydrolase domain containing 14B; NCBI GI:14249382);
CPNE1_HUMAN (copine I; NCBI GI:4503013);
SPEB_HUMAN (agmatinase; NCBI GI:18031951);
CK054_HUMAN (proteasome activator hPA28 subunit beta; NCBI GI:48257065);
BHMT2_HUMAN (betaine-homocysteine methyltransferase 2; NCBI GI:13162290);
MCCC2_HUMAN (methylcrotonoyl-Coenzyme A carboxylase 2 (beta); NCBI GI:11545863);
DBLOH_HUMAN (DIABLO protein; NCBI GI:13325198);
TMOD3_HUMAN (tropomodulin3; NCBI GI:6934244);
VPS29_HUMAN (vacuolar protein sorting 29 isoform 1; NCBI GI:7706441);
GRHPR_HUMAN (glyoxylate reductase/hydroxypyruvate reductase, isoform
CRA_a; NCBI GI:119578687);
PCYOX_HUMAN (prenylcysteine oxidase 1; NCBI GI:6561481); 및
PSME2_HUMAN (proteasome activator hPA28 subunit beta; NCBI GI:1008915).

The level of hepatocellular carcinoma tissues can be classified into 4 levels depending on their degree of differentiation as outlined by Edmondson and Steiner. When tumor cells are well-differentiated, not clearly distinguishable from normal liver cells, and composed of thin cords, these tumor cells are labeled as Edmondson grade 1 (E1). When tumor cells have relatively large nuclei and stained strongly with many cords, these tumors are labeled as Edmondson grade 2 (E2). When tumor cells are even larger with many macro cells, these tumors are labeled as Edmondson grade 3 (E3). When the differentiation of tumor cells are very poor such that almost all tumor cells have large and strongly stained nuclei, lose adhesiveness and are packed tightly, these tumors are labeled as Edmondson grade 4 (E4). The research described in present invention analyzed E1 and E2 hepatocellular carcinoma tissues.

Proteomic marker for early detection of liver cancer' in the present invention refers to materials that can discriminate early-stage HCC tissues and normal liver tissues, of which the major components are proteins. These proteomic markers in the present invention show characteristically high or low abundance in early-stage HCC tissues compared with the expression levels in normal liver tissues. Specifically, the proteomic markers in the present invention show fold-changes of greater than or equal to 1.5 fold or less than or equal to −1.5 fold in early-stage HCC tissues compared to the expression levels in normal liver tissues.

The present invention analyzed proteome from early stage hepatocellular carcinoma tissues, the protein markers thus identified is specific for early stage HCC, and thus they can be useful for early diagnosis of HCC. Further, considering the fact that these identified these proteomic markers show distinguishable changes in early stage of hepatocellular carcinoma, it is plausible that the physiological functions of these proteins are directly related to hepatocarcinogenesis. Therefore, these proteomic markers can be useful as target proteins for the study of the mechanism of hepatocarcinogensis and for developing liver cancer drugs.

The first aspect of the present invention is the proteomic marker for early detection of liver cancer. It is developed from proteome analysis of early hepatocellular carcinoma tissues such that these markers are much more useful than existing liver cancer markers analyzed only at DNA and mRNA levels. In addition, these markers are and much more valuable as treatment targets than existing liver cancer markers because of their specificity in early hepatocellular carcinoma.

The second aspect of the present invention relates to compositions for diagnosis of liver cancer, the compositions comprising the materials that can detect the presence, expression levels, and/or expression patterns of proteomic markers.

The specific detection of presence and expression levels and/or patterns of proteomic markers for early detection of liver cancer in the present invention is a process of confirming the presence and the expression level and/or patterns of proteomic markers within biological material. For instance, specific antibodies that bind to above early diagnostic markers of HCC could be used to detect the presence or expression level and/or patterns of proteomic markers. 'Biological material' in the present invention refers to cells or tissues that include but are not limited to urine, blood, plasma, and serum where the presence or expression level and/or patterns of proteomic markers can be detected. Further, 'antibody' in the present invention means proteins that specifically bind to epitopes, including polyclonal antibody, monoclonal antibody, and recombinant antibody.

Methods of detecting protein expression levels and/or patterns using antibodies include but are not limited to western blot, ELISA (enzyme linked immunosorbent assay), Radioimmunoassay, radioimmunodiffusion, Ouchterlony immunodiffusion analysis, rocket immunoelectrophoresis, immunohistochemistry, immunoprecipitation assay, Complement Fixation Assay, FACS (fluorescent activated cell sorter), and protein chip.

Through these analytic methods, the levels of antigen-antibody complexes in biological material from normal person and biological material from patients at risk of liver cancer can be compared, and the expression levels and/or patterns of proteomic markers for early stage liver cancer could be determined, ultimately making it possible to diagnose liver cancer for patients at risk at early stage.

'Antigen-antibody complex' in the present invention refers to the protein complex resulting from binding of specific antibody to early detection markers of liver cancer. The amount and pattern of the complex can be measured by the levels and patterns of signals from detection labels of secondary antibodies. These detection labels include but are not limited to enzymes, fluorescent materials, ligands, luminescent materials, microparticles, redox molecules, and radioisotopes. The enzymes for detection label include but are not limited to β-glucuronidase, β-D-glucurosidase, β-D-galactosidase, urease, peroxidase, alkaline phosphatase, acetylcholinesterase, glucose oxidase, hexokinase, GDPase, RNase, luciferase, phosphofructokinase, phosphoenol pyruvate, carboxylase, aspartate aminotransferase, phosphenolpyruvate decarboxylase, and □-lactamase. The fluorescence labels that can be used for detection label include but are not limited to fluorescein, isothiocyanate, rhodamine, phycoerythrin, phycocyanin, allophycocyanin, o-Phthaldehyde, and fluorescamine. The ligands for detection label include but are not limited to biotin derivative. The luminescent materials that can be used for detection label include but are not limited to acrininum ester, luciferin, and luciferase. The microparticles that can be used for detection label include but are not limited to nanogold and colored latex. The redox molecules that can be used for detection label include but are not limited to ferrocene, ruthenium complex, viologen, quinine, Ti ion, Cs ion, diimide, 1,4-benzoquinone, hydroquinone, K4W(CN)8, [Os(bpy)3]2+, [RU(bpy)3]2+, and [MO(CN)8]4–. The radioisotopes that can be used for detection label include but are not limited to 3H, 14C, 32P, 35S, 36C1, 51Cr, 57Co, 58Co, 59Fe, 90Y, 125I, 131I, and 186Re.

'The material that specifically detect the presence and expression levels and/or patterns of proteomic marker for early detection of liver cancer' in the second aspect of the present invention include any material that can be used to specifically detect the presence and expression levels and/or patterns of proteomic marker for early detection of liver cancer and are not limited to antibodies. The technological characteristics of the second aspect of the present invention lie in the specific detection of the presence and expression levels and/or patterns of proteomic marker for early detection of liver cancer such that any material that enables specific detection of the presence and expression levels and/or patterns of proteomic marker for early detection of liver cancer can be used as 'the material that specifically detect the presence and expression levels and/or patterns of proteomic marker for early detection of liver cancer' and achieves the intended technological effects. The skilled man in the art can select and use appropriate materials for specific embodiments based on well known techniques and knowledge in the field.

The third aspect of the present invention relates to compositions for early detection of liver cancer that specifically detect the presence and expression levels and/or patterns of genes that code the proteomic marker of the first aspect for early detection of liver cancer.

The presence and expression levels and/or patterns of proteomic markers for early detection of liver cancer in the present invention can be detected by using a method which detects proteins themselves as in the second aspect of the present invention, as well as a method that detects the presence and expression levels and/or patterns of genes that code these proteomic markers to conjecture the presence and expression levels and/or patterns of the proteomic markers for early detection of liver cancer.

The detection method of the presence and expression levels and/or patterns of genes typically use procedures which detect the presence and expression levels and/or patterns of mRNAs transcribed from these genes. The analytical methods that detect presence and expression levels and/or patterns of mRNAs include but are not limited to RT-PCR, competitive RT-PCR, real-time RT-PCR, RNase protection assay, northern blot, and DNA chip.

Through these analytic methods, the levels of mRNAs in biological material from normal person and biological material from patients at risk of liver cancer can be compared, and the expression levels and/or patterns of mRNAs that code the proteomic markers for early stage liver cancer can be determined, ultimately making it possible to diagnose the early stage liver cancer for patients at risk.

The kits to detect presence and expression levels and/or patterns of mRNAs through RT-PCR include specific primers that target mRNAs code for the proteomic markers for detection of early stage HCC of the present invention. 'Primer' in the present invention refers to nucleic acid sequences with complementary sequences to templates that allow for hybridization to templates and the free 3'hydroxyl groups that allow initiation of replication of templates by reverse transcriptase or DNA polymerase. Primers are nucleotides ranging from 7 to 50 bases, desirably between 10 and 30 bases, that have complementary sequences to the specific sequences of genes. The specific embodiments of RT-PCR kits can include test tubes or appropriate containers, buffer solutions, dNTPs, enzymes such as Taq-polymerase, reverse transcriptase, DNase, RNase RNase inhibitor, DEPC-treated water, sterile water. Primers can be used to initiate DNA synthesis in the presence of appropriate buffer solutions including chemicals for polymerization (ie, DNA polymerase and reverse transcriptase), 4 dNTPs, and under appropriate temperatures.

The primers can include other nucleotide sequences that do not affect the basic property of primers that act as the start positions of DNA synthesis. Primers can be synthesized according to known chemical methods and can be further modified with several known methods.

'The material that specifically detect the presence and expression levels and/or patterns of genes the code the proteomic marker for early detection of liver cancer' in the third aspect of the present invention include any material that can be used to specifically detect the presence and expression levels and/or patterns of genes that code the proteomic marker for early detection of liver cancer and are not limited to primers for RT-PCR. The technological characteristics of the third aspect of the present invention lie in the specific detection of the presence and expression levels and/or patterns of genes that code the proteomic marker for early detection of liver cancer, and thus any material that allow specific detection of the presence and expression levels and/or patterns of genes that code the proteomic marker for early detection of liver cancer can be used as 'the material that specifically detect the presence and expression levels and/or patterns of genes coding for proteomic marker for early detection of liver cancer' and achieve the intended technological effects. The skilled person in the art can select and use appropriate materials for specific embodiments based on well known techniques and knowledge in the field.

The fourth aspect of the present invention relates to liver cancer detection kits that include compositions for early detection of liver cancer in the second and third aspects of the present invention.

The diagnostic kits for liver cancer in the present invention can include one or more further materials, solutions, and devices suitable to detect the presence and expression levels and/or patterns of proteomic markers and genes that code the proteomic markers for early detection of liver cancer other than the materials included in the compositions for diagnosis of liver cancer that detect the presence and expression levels and/or patterns of proteomic markers and genes coding proteomic markers for early detection of liver cancer. For instance, if the above detection kits are kits for detecting presence and expression levels and/or patterns of proteins, the specific embodiments of these kits can include essential components of ELISA (enzyme linked immunosorbent assay), and these ELISA kits can include specific components to detect antibody-antigen complexes, for example, labeled secondary antibodies, chromophores, enzymes (for instance, antibody-linked enzymes) and substrates, and specific antibodies to quantify control proteins. On the other hand, if the above detection kits are kits for detecting presence and expression levels and/or patterns of genes, these detection kits can include specific components for RT-PCR, and the specific embodiments of RT-PCR kits can include test tubes or appropriate containers, buffer solutions, dNTPs, enzymes such as Taq-polymerase, reverse transcriptase, DNase, RNase RNase inhibitor, DEPC-treated water, sterile water, and specific primers for control genes. The specific embodiments of above kits for detection of liver cancer can include DNA chips or protein chips.

The fifth aspect of the present invention relates to a diagnostic method of diagnosing liver cancer that includes the first stage where the biological material from patients at risk of liver cancer are treated with the compositions of the second aspect of the present invention, and the second stage where the results of the first stage are compared with the results of the control groups to detect the presence and expression levels and/or patterns of proteomic markers for early detection of liver cancer in the first aspect of the present invention. Further, the fifth aspect of the present invention relates to a diagnostic method of diagnosing liver cancer that includes the first stage where the biological material from patients at risk of liver cancer are treated with the compositions of the third aspect of the present invention, and the second stage where the results of the first stage are compared with the results of the control groups to detect the presence and expression levels and/or patterns of genes coding proteomic markers for early detection of liver cancer in the first aspect of the present invention.

In case of detecting the presence and expression levels and/or patterns of the proteomic diagnostic markers for liver cancer whose expression levels are higher in early-stage HCC tissues than in normal liver tissues, for instance, the increased expression of these markers in the biological material from patients at risk of liver cancer, compared with that of the control group, indicates the possibility of liver cancer. On the other hand, in case of detecting the presence and expression levels and/or patterns of the proteomic diagnostic markers for liver cancer whose expression levels are lower in early-stage HCC tissues than in normal liver tissues, for instance, the decreased expression of these markers in the biological material from patients at risk of liver cancer, compared with that of the control group, indicates the possibility of liver cancer.

Further, in case of detecting the presence and expression levels and/or patterns of genes coding proteomic diagnostic markers for liver cancer whose expression levels are higher in early-stage HCC tissues than in normal liver tissues, for instance, the increased expression of mRNAs transcribed from these genes coding the proteomic markers in the biological material from patients at risk of liver cancer, compared with that of the control group, indicates the possibility of liver cancer. On the other hand, in case of detecting the presence and expression levels and/or patterns of genes coding proteomic diagnostic markers for liver cancer whose expression levels are lower in early-stage HCC tissues than in normal liver tissues, for instance, the decreased expression of mRNAs transcribed from these genes coding the proteomic markers in the biological material from patients at risk of liver cancer, compared with that of the control group, indicates the possibility of liver cancer.

The sixth aspect of the present invention relates to methods of screening therapeutic drugs for liver cancer that include the first stage where the test compounds are hybridized with proteomic markers for early detection of liver cancer, and the second stage that confirms whether the physiological activities of the above protein markers can be promoted or suppressed by the test compound.

The proteomic markers for early detection of liver cancer according to the first aspect of present invention relates to diagnostic markers of early HCC and these proteomic markers show distinguishable changes in early stage of hepatocellular carcinoma, making it plausible that the physiological functions of these proteins are relevant to hepatocarcinogenesis. Therefore, these proteomic markers can be useful as target proteins for mechanistic study of hepatocarcinogensis and for developing liver cancer drugs. That is, the first aspect of the present invention solves the problem on the important premise in the development of therapeutic drugs of liver cancer, and therefore, the screening methods for therapeutic drugs of liver cancer using these proteomic markers are within the scope of the present invention.

The methods of screening the therapeutic drugs of liver cancer can use known techniques such as affinity column purification where the proteomic markers of the first aspect of the present invention are fixed on affinity columns and hybridized with test samples [Pandya et al, Virus Res 87: 135-143, 2002], two-hybrid method [Fields, S and Song, O., Nature 340: 245-246, 1989], western blot ["Molecular Cloning—A Laboratory Manual" Cold Spring Harbor Laboratory, NY, Maniatis, T. at al. (1982) section 18.30-18.74], high-throughput screening [Aviezer et al, J Biomol Screen 6: 171-7, 2001]. The skilled person can choose appropriate methods for specific embodiments. The test samples used for screening include but are not limited to tissue extracts, expression products of gene libraries, synthetic compounds, synthetic peptides, and natural compounds.

The seventh aspect of the present invention relates to antibodies that specifically detect the proteomic markers of liver cancer in the first aspect of the present invention.

These antibodies are representative of materials that specifically detect the presence and expression levels and/or patterns of the proteomic markers for early detection of liver cancer, and therefore are useful material for early detection of liver cancer. Further, there are cases when these antibodies can repress or activate the activities of proteins related to hepatocarcinogenesis that are overexpressed and underexpressed in early-stage HCC, and therefore, can be used as therapeutic drugs for liver cancer.

Because the proteomic marker for the early detection of liver cancer has been provided in the first aspect of the present invention, polyclonal antibodies, monoclonal antibodies, and recombinant antibodies can be routinely produced according to well known techniques in the field.

Polyclonal antibodies can be produced by known techniques such as collecting antibody containing serum from the blood drawn from animals injected with proteomic marker antigens for early detection of liver cancer in the first aspect of the present invention. These polyclonal antibodies can be produced from diverse animal hosts such as goats, rabbits, lambs, monkeys, horses, pigs, cows, dogs and these techniques are well known in the field.

Monoclonal antibody can be produced according to known techniques such as hybridoma method (Kohler and Milstein (1976) European Journal of Immunology 6:511-519) or phage antibody libraries (Clackson et al, Nature, 352:624-628, 1991; Marks et al, J. Mol. Biol., 222:58, 1-597, 1991). Generally, hybridoma technique uses cells from host animals inoculated with antigens of proteomic markers for early detection of liver cancer in the first aspect of the present invention, and cancer or melanoma cell lines. These two types of cells can be fused by known techniques such as polyethylene glycol method and these antibody-producing cells are proliferated by standard tissue culture methods. Uniform cell colonies are acquired by subcloning with limited dilution technique and these hybridoma cells that produce desired antibodies are cultured in larger scale in vitro or in vivo.

Phage antibody library method is the method where the genes coding for desired antibodies are expressed and the antibodies are displayed on the surface of phage as recombinant proteins such that antibody libraries are created in vitro and desired monoclonal antibodies are purified from these libraries for production. Monoclonal antibodies thus created can be purified by known techniques such as gel electrophoresis, dialysis, salt precipitation, ion exchange chromatography, and affinity chromatography.

The seventh aspect of the present invention includes a complete form of antibody with two light chains and two heavy chains, and functional fragments. Functional antibody fragments mean the fragments with epitope binding ability, for instance, Fab, F(ab'), F(ab')2, and Fv.

EXPERIMENTAL EXAMPLES

The specific examples listed below are solely to improve the understanding of the present invention and do not limit its scope in any way.

Example 1

Total Protein Extraction from Clinical Samples and Quantitation

Two E1 grade HCC tissues, four E2 grade HCC tissues, and five surrounding normal livers were acquired from five HCC patients. Eleven sets of total protein samples from each clinical specimen were acquired as follows:

Tissues were washed with 1×PBS, and grinded with mixed buffer [Buffer A (Deionized water 100 ml, Tris (50 mM) 0.606 g, KCl (100 mM) 0.746 g, Glycerol (20%) 20 g, pH 7.1), Protease inhibitor 1A (buffer A 2 ml, complete mini (protease inhibitor cocktail) one tablet), and Protease inhibitor 1B (Pepstatin A (9.603 mg in 100 mL EtOH) 10 ml(=1.4 μM), PMSF (Phenylmethylsulfonyl fluoride, 1.742 g in 100 mL) 10 ml (=1.0 mM))]. The ground-up tissues were sonicated and ultra-centrifuged (50,000 rpm) at 4 □ for 1 hr. Ten ml of the supernatant was precipitated with TCA (10% TCA precipitation) to precipitate protein pellets. The remaining supernatant was labeled as supernatant 1. Also, the protein pellets were dissolved in existing supernatants and mixed buffer [Buffer A (Deionized water 100 ml, Tris (50 mM) 0.606 g, KCl (100 mM) 0.746 g, Glycerol (20%) 20 g, pH 7.1), Protease inhibitor 1A (buffer A 2 ml, complete mini (protease inhibitor cocktail) one tablet), and Protease inhibitor 1B (Pepstatin A (9.603 mg in 100 mL EtOH) 10 ml(=1.4 μM), PMSF (Phenylmethylsulfonyl fluoride, 1.742 g in 100 mL) 10 ml (=1.0 mM))], sonicated, and ultra-centrifuged (50,000 rpm) at 4 □ for 1 hr. Ten ml of the supernatant was precipitated to precipitate protein pellets with TCA (10% TCA precipitation). The remaining supernatant was labeled as supernatant 2. The resulting protein pellets were dissolved in 9/2/4 buffer [9 M Urea, 2M Thiourea, 4% CHAPS(+18 mM DTT)), Protease inhibitor 1A (buffer A 2 ml, complete mini (protease inhibitor cocktail) one tablet], and ultra-centrifuged (50,000 rpm) at 17 □ for 1 hr. The remaining supernatant was labeled as supernatant 3. The supernatant 1 and supernatant 2 were combined and relabeled as 'sup', and the supernatant 3 was relabeled as 'ppt'. For each tissue, sup and ppt were paired as a protein sample set. Bradford assay (5× Protein Assay from Biorad measured at 595 nm) was used to quantitate protein samples.

The protein yields from each tissue are listed in table 1.

TABLE 1

| | | Normal (Non-Tumor) | Tumor 1 | Tumor 2 |
|---|---|---|---|---|
| #1 (E2) | Tissue (g) | 0.59 | 0.34 | 0.235 |
| | soluble | total volume 2.9 ml protein 10 mg | total volume 0.85 ml protein 10 mg | total volume 0.75 ml protein 4.9 mg |
| | insoluble | total volume 1.8 ml protein 6.5 mg | total volume 1.2 ml protein 4 mg | total volume 0.9 ml protein 3.4 mg |
| #13 (E1) | Tissue (g) | 0.601 | 0.522 | |
| | soluble | total volume 1.75 ml protein 21.8 mg | total volume 1.33 ml protein 21.6 mg | |
| | insoluble | total volume 2.34 ml protein 8 mg | total volume 2.17 ml protein 7.6 mg | |
| #14 (E1) | Tissue (g) | 0.463 | 0.22 | |
| | soluble | total volume 0.78 ml protein 10.5 mg | total volume 0.95 ml protein 12.5 mg | |
| | insoluble | total volume 2.88 ml protein 8.9 mg | total volume 1.4 ml protein 5.3 mg | |
| #26 (E2) | Tissue (g) | 0.766 | 1.126 | |
| | soluble | total volume 2.97 ml protein 34.1 mg | total volume 4.3 ml protein 40.3 mg | |
| | insoluble | total volume 3.88 ml protein 11.48 mg | total volume 5.88 ml protein 20 mg | |
| #28 (E2) | Tissue (g) | 1.689 | 0.824 | |
| | soluble | total volume 4.1 ml protein 49.2 mg | total volume 1.3 ml protein 15.2 mg | |
| | insoluble | total volume 4 ml protein 12.9 mg | total volume 4.3 ml protein 7 mg | |

Example 2

2-Dimensional PAGE

For 11 sets of total protein samples acquired in example 1, 2-dimensional SDS-PAGE was performed as follows:

300 μg of sup and ppt were sampled and mixed with 1 M DTT 6.3 μl (=18 mM DTT), IPG buffer 7 μl (=2%), and BPB (Bromophenol Blue) 2 μl, and further mixed with 9/2/4 buffer [(9 M urea, 2 M thiourea, 4% CHAPS(+18 mM DTT))] to a final volume of 350 μl. The samples were then loaded on a rehydration tray with IPG strip (immobilized pH gradient gel strip) and rehydrated for 12 hrs. The rehydrated IPG strip was subjected to IEF (isoelectric focusing) (500 V, 2 mA, 5 W, 1 min; 3500 V, 2 mA, 5 W, 1 hr 30 min; 3500 V, 2 mA, 5 W, 10 hrs). After IEF, IPG strip was equilibrated, washed with deionized water, loaded on a SDS-PAGE, and subjected to electrophoresis at 40 mA. After electrophoresis, the gel was silver stained [Silver nitrate (2.5% w/v)] and the gel image was acquired. The image was analyzed in progenesis samespot program (NonLinear) to align protein spots and calculate fold changes.

Figure 2:
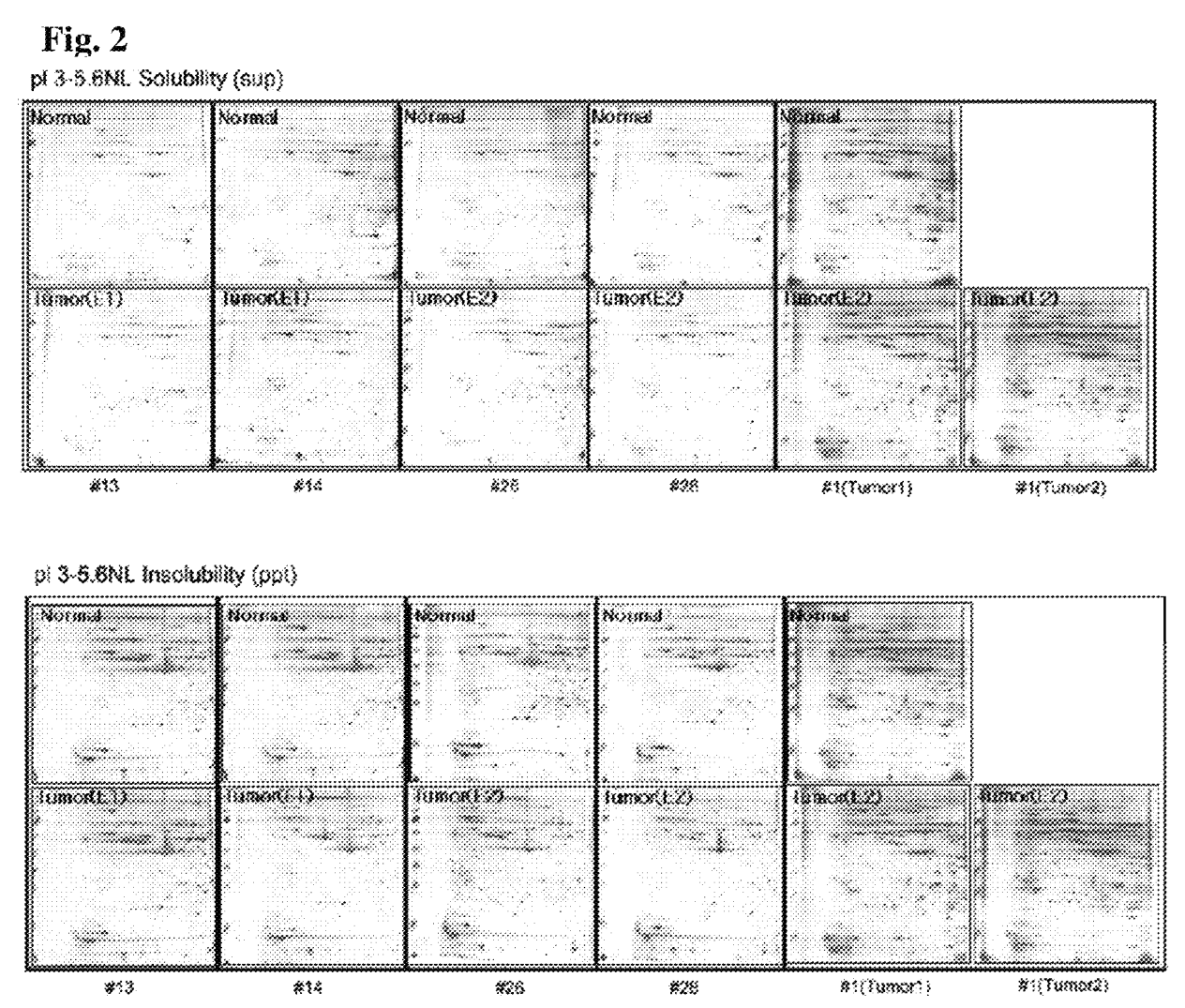
Figure 3:
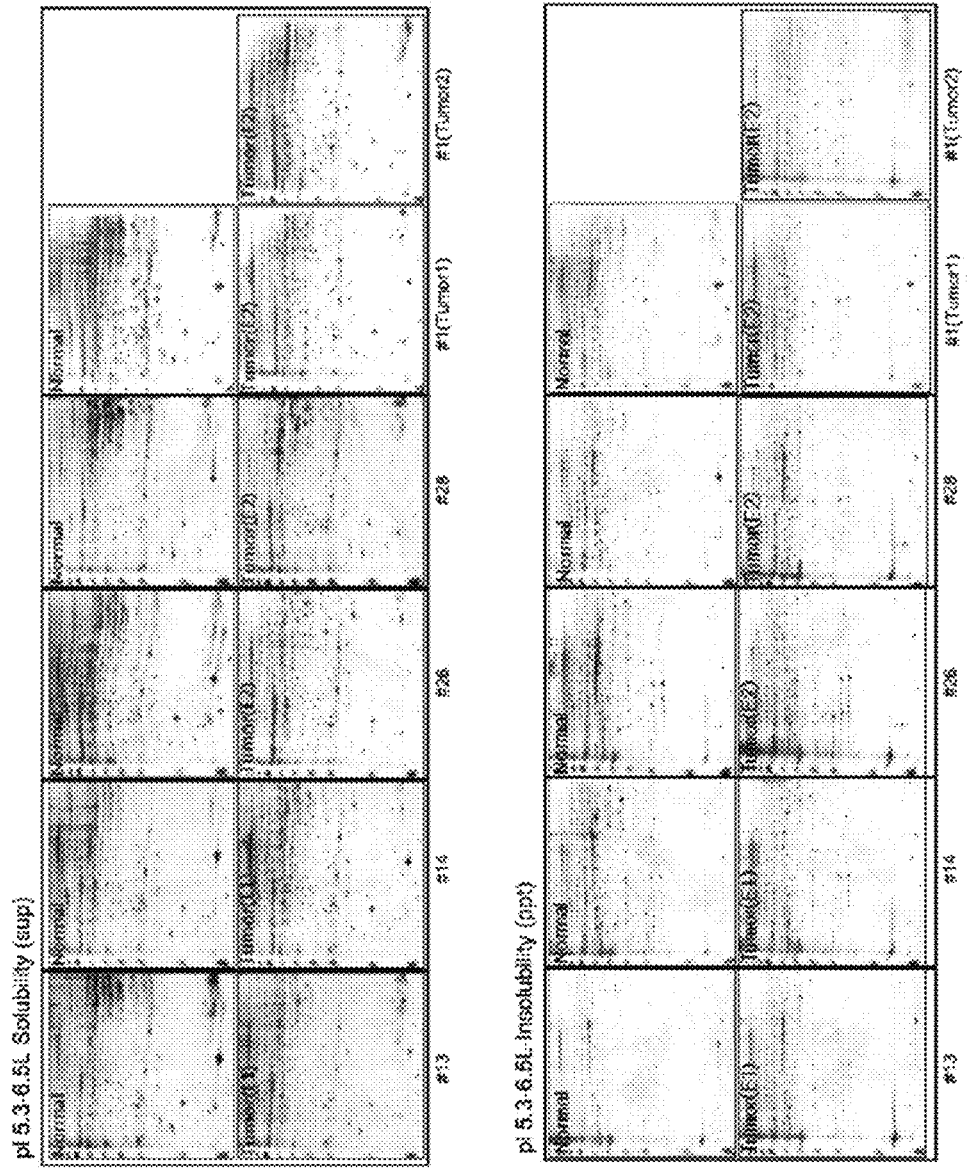
FIG. 3. 2D Gel images (pI 5.3-6.5 L) of Edmondson grade I hepatocellular carcinoma tissues (n=2), Edmondson grade II hepatocellular carcinoma tissues (n=4), and surrounding noncancerous tissues (n=5).
Figure 4:
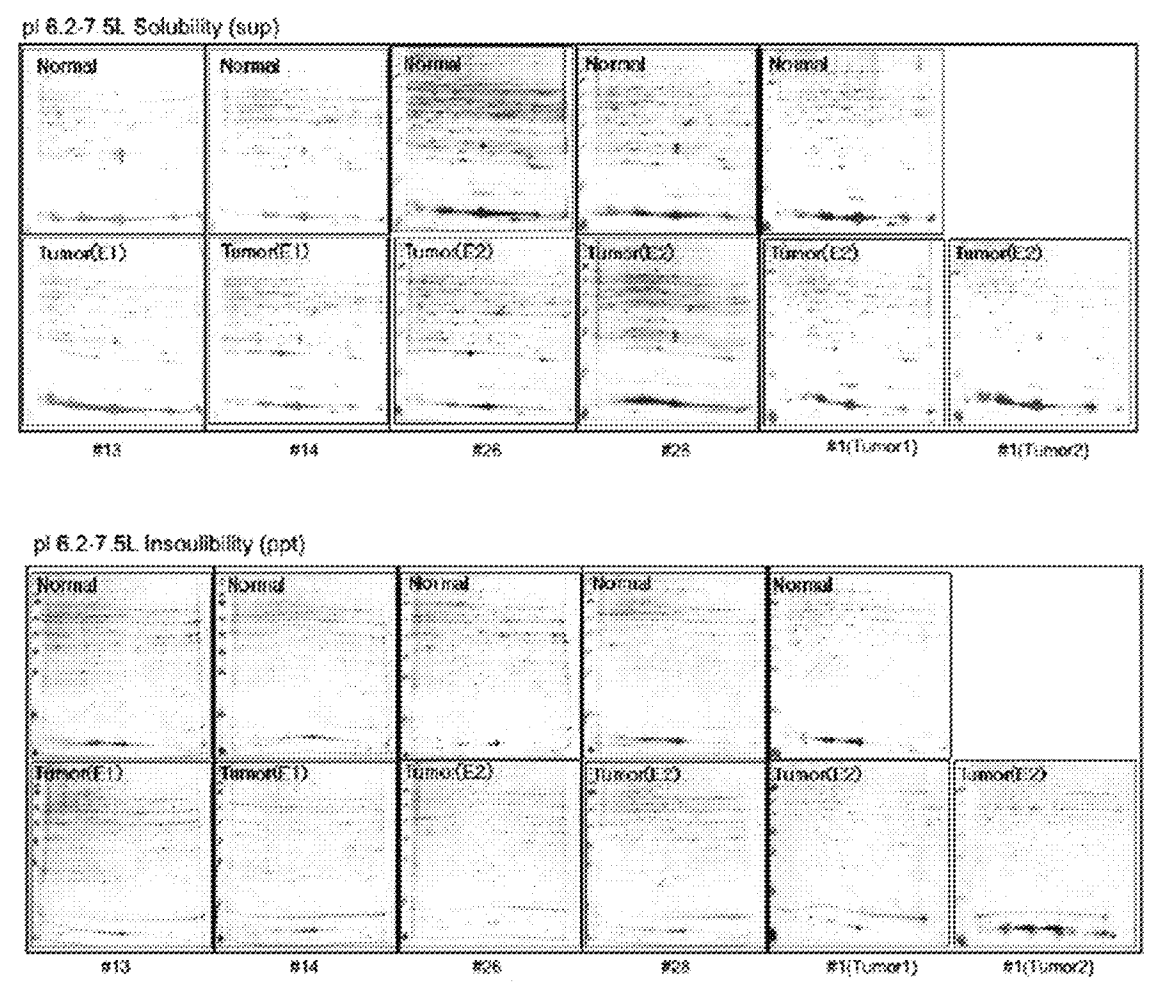

The acquired images are shown in FIG. 1 (pI 3-11), FIG. 2 (pI 3-5.6), FIG. 3 (pI 5.3-6.5), and FIG. 4 (pI 6.2-7.5). These images clearly show that the proteome from E1 and E2 HCC tissues are significantly different from the proteome of normal liver tissues.

Example 3

Protein Identification by MS Analysis

For each protein spot in example 2, protein was identified as follows:

Each protein spot was excised from electrophoresis gel, washed with destaining solution (1:1 mixture of 30 mM potassium ferricyanide and 100 mM sodium thiosulfate) and dried. Then, proteolysis solution was added (5-10 ng/μl trypsin 1 μl and 50 mM ammonium bicarbonate 19 μl) and incubated overnight at 37 □ for peptidization of proteins.

The peptides were extracted three times with 10~20 μl of extraction solution (50% acetonitrile+5% trifluoroacetic acid) and concentrated to 4~5 μl. Then, it was mixed with 1 μl matrix solution (50% v/v acetonitrile, alpha-4-cyano-hydroxycinnamic acid 10 mg/ml, 0.1% TFA), adsorbed to MALDI-MS plate, dried, and analyzed by ABI explorer 4700 with MALDI-TOF and MALDI-TOF/TOF methods to determine peptide masses. The peptide masses were searched through protein database program (Mascot and ProbePMF) to identify proteins.

The identified proteins were sorted by their fold-changes as calculated in example 2, and 70 novel proteins from E1 HCC tissues and 77 novel proteins from E2 HCC tissues were identified with fold change greater than or equal to 1.5 fold, or less than or equal to −1.5 fold. The results are shown in table 2 through table 7. Table 2 and table 3 list proteins from E1 HCC tissues with fold change greater than or equal to 1.5 fold or less than or equal to −1.5 fold. Table 4 and table 5 list proteins from E2 HCC tissues with fold change greater than or equal to 1.5 fold or less than or equal to −1.5 fold. Table 6 and table 7 list proteins from E1 and E2 HCC tissues with average fold change greater than or equal to 1.5 fold or less than or equal to −1.5 fold. In the table, 'E1' indicates the average fold change in 2 E1 HCC tissues, 'E2' indicates the average fold change in 4 E2 HCC tissues, and 'ave' indicates average fold change in 2 E1 HCC tissues and 4 E2 HCC tissues.

TABLE 2

| Uniprot ID | NCBI GI | E1 | E2 | 평균 | Mw | pI |
|---|---|---|---|---|---|---|
| A1XP52_HUMAN | 94450030 | 2.38 | 2.05 | 2.16 | 25 | 5.7 |
| NDUS3_HUMAN | 4758788 | −3.94 | −2.45 | −2.95 | 26 | 5.6 |
| ATP5H_HUMAN | 5453559 | −2.07 | −2.44 | −2.32 | 22 | 5.1 |
| ERLN2_HUMAN | 6005721 | −2.38 | −2.44 | −2.42 | 42 | 5.6 |
| SNP29_HUMAN | 4759154 | −3.37 | −1.29 | −1.98 | 30 | 5.6 |
| AIFM1_HUMAN | 22202629 | −1.58 | −0.54 | −0.88 | 62 | 7.2 |
| ADA_HUMAN | 47078295 | −3.35 | 0.29 | −0.92 | 43 | 5.6 |
| CO3_HUMAN | 78101268 | 1.91 | 0.14 | 0.73 | 115 | 5.6 |
| APOA1_HUMAN | 119587681 | −3.46 | −4.49 | −4.15 | 25 | 5.3 |
| FRIH_HUMAN | 76779199 | −3.00 | −1.30 | −1.86 | 20 | 5.2 |
| ARLY_HUMAN | 18033920 | 1.91 | −1.82 | −0.58 | 48 | 6.0 |
| APT_HUMAN | 4502171 | −3.80 | −0.51 | −1.61 | 20 | 5.5 |
| HSP71_HUMAN | 147744565 | −2.67 | 0.19 | −0.77 | 69 | 5.4 |
| ADH4_HUMAN | 83286923 | −2.54 | −1.15 | −1.61 | 26 | 8.3 |
| VILI_HUMAN | 6005944 | −3.24 | 2.78 | 0.77 | 90 | 6.1 |
| PYC_HUMAN | 106049292 | −1.63 | 0.03 | −0.52 | 122 | 6.2 |
| TCTP_HUMAN | 4507669 | 5.76 | 1.56 | 2.96 | 22 | 4.7 |
| PLSL_HUMAN | 4504965 | 2.19 | 1.73 | 1.88 | 69 | 5.3 |
| ACPH_HUMAN | 23510451 | −1.55 | 0.14 | −0.42 | 78 | 5.3 |
| GLNA_HUMAN | 22749655 | 1.98 | −0.10 | 0.59 | 50 | 5.8 |
| AK1C4_HUMAN | 1705823 | −4.37 | −2.47 | −3.11 | 35 | 6.3 |
| TCPA_HUMAN | 57863257 | 2.47 | 0.86 | 1.39 | 66 | 5.8 |
| VINC_HUMAN | 4507877 | −1.50 | 0.43 | −0.21 | 47 | 5.7 |
| TYPH_HUMAN | 4503445 | 2.76 | −0.04 | 0.89 | 53 | 5.3 |
| IREB1_HUMAN | 8659555 | −2.08 | −4.52 | −3.71 | 100 | 6.3 |
| TGM2_HUMAN | 39777597 | −3.50 | −2.08 | −2.55 | 69 | 5.9 |
| CPT2_HUMAN | 4503023 | −1.59 | −0.37 | −0.78 | 66 | 7.5 |
| MOES_HUMAN | 4505257 | 1.97 | 0.62 | 1.07 | 70 | 6.2 |

TABLE 2-continued

| Uniprot ID | NCBI GI | E1 | E2 | 평균 | Mw | pI |
|---|---|---|---|---|---|---|
| EF1G_HUMAN | 119594432 | −1.67 | 1.09 | 0.17 | 48 | 6.2 |
| AOFB_HUMAN | 38202207 | −3.59 | −0.98 | −1.85 | 60 | 6.5 |
| 1433T_HUMAN | 5803227 | 3.95 | 1.67 | 2.43 | 28 | 4.6 |
| PSB9_HUMAN | 23110932 | 5.71 | 0.38 | 2.16 | 20 | 4.6 |
| 2AAA_HUMAN | 149243188 | 2.07 | 0.76 | 1.20 | 65 | 5.0 |
| QCR1_HUMAN | 46593007 | 1.53 | −0.00 | 0.51 | 52 | 5.9 |
| 1433B_HUMAN | 4507949 | 3.02 | 2.11 | 2.42 | 28 | 4.7 |
| PRDX2_HUMAN | 32189392 | −3.59 | −1.69 | −2.32 | 23 | 5.5 |
| ACSL1_HUMAN | 40807491 | −2.79 | −0.68 | −1.39 | 66 | 6.4 |
| PHB_HUMAN | 4505773 | −14.89 | −0.98 | −5.62 | 28 | 5.6 |
| ODO2_HUMAN | 643589 | 1.87 | −1.24 | −0.20 | 55 | 5.8 |
| LPPRC_HUMAN | 31621305 | 1.85 | −2.32 | −0.93 | 140 | 5.6 |

TABLE 3

| Uniprot ID | NCBI GI | E1 | E2 | 평균 | Mw | pI |
|---|---|---|---|---|---|---|
| CAZA2_HUMAN | 433308 | −1.98 | −2.05 | −2.03 | 35 | 5.6 |
| UCRI_HUMAN | 5174743 | −1.56 | 0.21 | −0.38 | 23 | 6.3 |
| AL9A1_HUMAN | 62511242 | 1.64 | 0.71 | 1.02 | 50 | 5.5 |
| HINT1_HUMAN | 4885413 | −1.54 | 0.04 | −0.49 | 13 | 6.3 |
| SSRD_HUMAN | 5454090 | 2.26 | 6.74 | 5.25 | 18 | 5.6 |
| SNAA_HUMAN | 47933379 | −1.53 | 0.60 | −0.11 | 33 | 5.2 |
| TERA_HUMAN | 6005942 | 1.62 | 1.22 | 1.35 | 93 | 5.3 |
| 1433E_HUMAN | 5803225 | 2.22 | 0.60 | 1.14 | 27 | 4.4 |
| 1433Z_HUMAN | 4507953 | 2.93 | 1.78 | 2.17 | 28 | 4.6 |
| SKP1_HUMAN | 25777713 | 2.41 | 1.07 | 1.52 | 19 | 4.2 |
| ACTG_HUMAN | 15277503 | 2.12 | 0.77 | 1.22 | 93 | 5.3 |
| TCPB_HUMAN | 48146259 | 1.68 | 1.54 | 1.59 | 51 | 6.0 |
| SET_HUMAN | 145843637 | 5.59 | 1.63 | 2.95 | 20 | 4.8 |
| LGUL_HUMAN | 118402586 | 2.39 | 0.78 | 1.32 | 22 | 4.9 |
| ST2A1_HUMAN | 29540545 | −4.66 | −2.90 | −3.48 | 33 | 5.4 |
| PRDX4_HUMAN | 5453549 | −1.57 | 1.68 | 0.60 | 26 | 5.6 |
| FCL_HUMAN | 4507709 | 1.64 | 1.99 | 1.87 | 42 | 6.2 |
| GANAB_HUMAN | 2274968 | 2.01 | −2.09 | −0.72 | 113 | 5.7 |
| UGPA_HUMAN | 2136353 | −2.45 | −2.34 | −2.38 | 55 | 7.4 |
| TOIP1_HUMAN | 119611474 | −1.61 | −3.38 | −2.79 | 63 | 6.0 |
| Q5U0A0_HUMAN | 54696300 | 2.48 | 0.14 | 0.92 | 25 | 4.6 |
| HIBCH_HUMAN | 3320120 | −2.18 | −0.96 | −1.36 | 39 | 6.7 |
| DCXR_HUMAN | 7705925 | −1.51 | −1.75 | −1.67 | 25 | 10.1 |
| PTOV1_HUMAN | 7920398 | −1.54 | −1.38 | −1.43 | 32 | 9.3 |
| ABHEB_HUMAN | 14249382 | 2.34 | −2.74 | −1.05 | 24 | 5.8 |
| CPNE1_HUMAN | 4503013 | 1.56 | 0.75 | 1.02 | 64 | 5.5 |
| SPEB_HUMAN | 18031951 | 4.08 | −0.14 | 1.27 | 32 | 5.8 |
| MCCC2_HUMAN | 11545863 | 1.51 | 0.60 | 0.91 | 58 | 6.5 |
| DBLOH_HUMAN | 13325198 | 3.77 | 0.89 | 1.85 | 19 | 4.8 |
| PCYOX_HUMAN | 6561481 | −3.43 | −0.58 | −1.53 | 59 | 6.6 |

TABLE 4

| Uniprot ID | NCBI GI | E1 | E2 | 평균 | Mw | pI |
|---|---|---|---|---|---|---|
| A1XP52_HUMAN | 94450030 | 2.38 | 2.05 | 2.16 | 25 | 5.7 |
| ARSA1_HUMAN | 50428938 | 0.14 | 1.69 | 1.17 | 41 | 4.9 |
| MAAI_HUMAN | 3510757 | 1.49 | −4.09 | −2.23 | 23 | 6.2 |
| UGDH_HUMAN | 4507813 | −0.03 | 1.82 | 1.20 | 58 | 6.9 |
| NDUS3_HUMAN | 4758788 | −3.94 | −2.45 | −2.95 | 26 | 5.6 |
| FTHFD_HUMAN | 3560541 | 1.33 | −2.97 | −1.54 | 102 | 5.6 |
| ATP5H_HUMAN | 5453559 | −2.07 | −2.44 | −2.32 | 22 | 5.1 |
| ERLN2_HUMAN | 6005721 | −2.38 | −2.44 | −2.42 | 42 | 5.6 |
| LDHA_HUMAN | 62897717 | −1.46 | −2.87 | −2.40 | 34 | 9.7 |
| LMNA_HUMAN | 5031875 | 2.24 | 5.12 | 4.16 | 63 | 6.3 |
| APOA1_HUMAN | 119587681 | −3.46 | −4.49 | −4.15 | 25 | 5.3 |
| ANXA1_HUMAN | 157829895 | −0.35 | −1.80 | −1.32 | 35 | 6.3 |
| ARLY_HUMAN | 18033920 | 1.91 | −1.82 | −0.58 | 48 | 6.0 |
| HS90B_HUMAN | 306891 | −1.95 | 1.99 | 0.68 | 86 | 5.1 |
| GSTA2_HUMAN | 257476 | 0.27 | −2.11 | −1.32 | 24 | 9.0 |
| VILI_HUMAN | 6005944 | −3.24 | 2.78 | 0.77 | 90 | 6.1 |
| ODB2_HUMAN | 179354 | 0.16 | −2.60 | −1.68 | 51 | 6.2 |
| PYC_HUMAN | 632808 | 1.46 | −1.95 | −0.82 | 115 | 6.2 |
| KU70_HUMAN | 4503841 | −1.23 | 1.80 | 0.79 | 69 | 6.2 |
| KU86_HUMAN | 10863945 | −1.60 | 2.03 | 0.82 | 75 | 5.7 |
| TCTP_HUMAN | 4507669 | 5.76 | 1.56 | 2.96 | 22 | 4.7 |

TABLE 4-continued

| Uniprot ID | NCBI GI | E1 | E2 | 평균 | Mw | pI |
|---|---|---|---|---|---|---|
| PLSL_HUMAN | 4504965 | 2.19 | 1.73 | 1.88 | 69 | 5.3 |
| AK1C4_HUMAN | 1705823 | -4.37 | -2.47 | -3.11 | 35 | 6.3 |
| TCPA_HUMAN | 57863257 | 1.21 | 1.69 | 1.53 | 61 | 5.8 |
| VINC_HUMAN | 7669550 | -0.05 | -6.54 | -4.38 | 132 | 5.9 |
| IREB1_HUMAN | 8659555 | -2.08 | -4.52 | -3.71 | 100 | 6.3 |
| ODBB_HUMAN | 7546385 | -0.45 | -2.22 | -1.63 | 38 | 5.4 |
| TGM2_HUMAN | 39777597 | -3.50 | -2.08 | -2.55 | 69 | 5.9 |
| EF1B_HUMAN | 4503477 | 1.21 | 1.66 | 1.51 | 28 | 4.3 |
| 1433T_HUMAN | 5803227 | 3.95 | 1.67 | 2.43 | 28 | 4.6 |
| TKT_HUMAN | 4507521 | 1.29 | 1.54 | 1.46 | 68 | 8.2 |
| AL4A1_HUMAN | 25777734 | 1.45 | -1.64 | -0.61 | 59 | 6.7 |
| ERP29_HUMAN | 5803013 | 1.44 | -4.07 | -2.23 | 26 | 5.7 |
| AL1B1_HUMAN | 25777730 | -0.05 | -1.85 | -1.25 | 54 | 6.1 |
| HNRH1_HUMAN | 5031753 | 1.03 | 2.22 | 1.82 | 52 | 4.8 |
| 1433B_HUMAN | 4507949 | 3.02 | 2.11 | 2.42 | 28 | 4.7 |
| PHB_HUMAN | 4505773 | -5.19 | -1.91 | -3.00 | 28 | 5.4 |
| CBS_HUMAN | 4557415 | -1.27 | -2.80 | -2.29 | 59 | 6.3 |
| MYH9_HUMAN | 189030 | 0.25 | 1.82 | 1.29 | 80 | 7.3 |
| ODO2_HUMAN | 499719 | -1.48 | 2.27 | 1.02 | 64 | 6.8 |

TABLE 5

| Uniprot ID | NCBI GI | E1 | E2 | 평균 | Mw | pI |
|---|---|---|---|---|---|---|
| PEX19_HUMAN | 4506339 | 0.79 | 2.51 | 1.94 | 36 | 4.2 |
| LPPRC_HUMAN | 31621305 | 1.85 | -2.32 | -0.93 | 140 | 5.6 |
| CAZA2_HUMAN | 433308 | -1.98 | -2.05 | -2.03 | 35 | 5.6 |
| TCPE_HUMAN | 24307939 | -0.13 | 1.59 | 1.02 | 62 | 5.5 |
| ST1A1_HUMAN | 847763 | -1.12 | -2.16 | -1.81 | 30 | 5.9 |
| SSRD_HUMAN | 5454090 | 2.26 | 6.74 | 5.25 | 18 | 5.6 |
| GDIR_HUMAN | 2624719 | -1.49 | -2.08 | -1.88 | 26 | 5.0 |
| KAD2_HUMAN | 7524346 | 0.16 | -2.14 | -1.37 | 28 | 7.8 |
| 1433Z_HUMAN | 4507953 | 2.93 | 1.78 | 2.17 | 28 | 4.6 |
| ACTG_HUMAN | 15277503 | 2.62 | -3.52 | -1.48 | 64 | 5.2 |
| HBB_HUMAN | 4504349 | 1.25 | 1.60 | 1.48 | 27 | 7.4 |
| TCPB_HUMAN | 48146259 | 1.68 | 1.54 | 1.59 | 51 | 6.0 |
| SET_HUMAN | 145843637 | 5.59 | 1.63 | 2.95 | 20 | 4.8 |
| MMSA_HUMAN | 11095441 | -0.04 | -1.51 | -1.02 | 57 | 7.5 |
| BDH_HUMAN | 17738292 | -0.07 | -2.38 | -1.61 | 29 | 8.1 |
| C1QBP_HUMAN | 1096067 | 0.50 | 2.03 | 1.52 | 32 | 4.3 |
| PRDX4_HUMAN | 5453549 | -1.57 | 1.68 | 0.60 | 26 | 5.6 |
| FCL_HUMAN | 4507709 | 1.64 | 1.99 | 1.87 | 42 | 6.2 |
| DPYS_HUMAN | 4503375 | 0.04 | -3.04 | -2.01 | 55 | 6.8 |
| MVP_HUMAN | 19913410 | -1.35 | 1.74 | 0.71 | 110 | 5.3 |
| IMMT_HUMAN | 516766 | 1.30 | -1.79 | -0.76 | 82 | 5.8 |
| GLE1_HUMAN | 4557627 | 1.46 | 3.79 | 3.01 | 18 | 5.1 |
| Q56G89_HUMAN | 62113341 | 0.48 | 1.59 | 1.22 | 68 | 5.6 |
| TOIP1_HUMAN | 119611474 | -1.61 | -3.38 | -2.79 | 63 | 6.0 |
| F108B_HUMAN | 71051602 | -1.23 | 1.56 | 0.63 | 42 | 6.3 |
| DCXR_HUMAN | 7705925 | -1.51 | -1.75 | -1.67 | 25 | 10.1 |
| GLCTK_HUMAN | 31543063 | 0.16 | -1.70 | -1.08 | 59 | 5.9 |
| CS010_HUMAN | 3355455 | -0.65 | -2.30 | -1.75 | 14 | 6.3 |
| FAH2A_HUMAN | 4929679 | -1.24 | -2.75 | -2.25 | 33 | 6.6 |
| ABHEB_HUMAN | 14249382 | 2.34 | -2.74 | -1.05 | 24 | 5.8 |
| CK054_HUMAN | 48257065 | -0.49 | -1.54 | -1.19 | 36 | 6.3 |
| BHMT2_HUMAN | 13162290 | 0.10 | -1.67 | -1.08 | 40 | 5.7 |
| TMOD3_HUMAN | 6934244 | -0.18 | -1.75 | -1.23 | 41 | 5.2 |
| VPS29_HUMAN | 7706441 | 0.07 | 2.02 | 1.37 | 21 | 6.3 |
| GRHPR_HUMAN | 119578687 | -0.47 | -1.80 | -1.36 | 34 | 6.4 |
| PCYOX_HUMAN | 115311617 | -0.06 | -1.57 | -1.06 | 60 | 5.9 |
| PSME2_HUMAN | 1008915 | 1.32 | -1.65 | -0.66 | 29 | 5.4 |

TABLE 6

| Uniprot ID | NCBI GI | E1 | E2 | 평균 | Mw | pI |
|---|---|---|---|---|---|---|
| A1XP52_HUMAN | 94450030 | 2.38 | 2.05 | 2.16 | 25 | 5.7 |
| MAAI_HUMAN | 3510757 | 1.49 | -4.09 | -2.23 | 23 | 6.2 |
| NDUS3_HUMAN | 4758788 | -3.94 | -2.45 | -2.95 | 26 | 5.6 |
| FTHFD_HUMAN | 21614513 | -2.28 | -1.89 | -2.02 | 53 | 5.4 |
| ATP5H_HUMAN | 5453559 | -2.07 | -2.44 | -2.32 | 22 | 5.1 |
| ERLN2_HUMAN | 6005721 | -2.38 | -2.44 | -2.42 | 42 | 5.6 |
| SNP29_HUMAN | 4759154 | -3.37 | -1.29 | -1.98 | 30 | 5.6 |

TABLE 6-continued

| Uniprot ID | NCBI GI | E1 | E2 | 평균 | Mw | pI |
|---|---|---|---|---|---|---|
| LDHA_HUMAN | 62897717 | -1.46 | -2.87 | -2.40 | 34 | 9.7 |
| LMNA_HUMAN | 5031875 | 2.24 | 5.12 | 4.16 | 63 | 6.3 |
| APOA1_HUMAN | 119587681 | -3.46 | -4.49 | -4.15 | 25 | 5.3 |
| FRIH_HUMAN | 76779199 | -3.00 | -1.30 | -1.86 | 20 | 5.2 |
| APT_HUMAN | 4502171 | -3.80 | -0.51 | -1.61 | 20 | 5.5 |
| ADH4_HUMAN | 83286923 | -2.54 | -1.15 | -1.61 | 26 | 8.3 |
| ODB2_HUMAN | 179354 | 0.16 | -2.60 | -1.68 | 51 | 6.2 |
| KU86_HUMAN | 10863945 | 2.03 | 1.41 | 1.61 | 90 | 5.6 |
| TCTP_HUMAN | 4507669 | 5.76 | 1.56 | 2.96 | 22 | 4.7 |
| PLSL_HUMAN | 4504965 | 2.83 | 1.18 | 1.73 | 68 | 5.2 |
| AK1C4_HUMAN | 1705823 | -4.37 | -2.47 | -3.11 | 35 | 6.3 |
| TCPA_HUMAN | 57863257 | 1.21 | 1.69 | 1.53 | 61 | 5.8 |
| VINC_HUMAN | 7669550 | -0.05 | -6.54 | -4.38 | 132 | 5.9 |
| IREB1_HUMAN | 8659555 | -2.08 | -4.52 | -3.71 | 100 | 6.3 |
| ODBB_HUMAN | 7546385 | -0.45 | -2.22 | -1.63 | 38 | 5.4 |
| TGM2_HUMAN | 39777597 | -3.50 | -2.08 | -2.55 | 69 | 5.9 |
| EF1B_HUMAN | 4503477 | 1.21 | 1.66 | 1.51 | 28 | 4.3 |
| AOFB_HUMAN | 38202207 | -3.59 | -0.98 | -1.85 | 60 | 6.5 |
| 1433T_HUMAN | 5803227 | 3.95 | 1.67 | 2.43 | 28 | 4.6 |
| PSB9_HUMAN | 23110932 | 5.71 | 0.38 | 2.16 | 20 | 4.6 |
| ERP29_HUMAN | 5803013 | 1.44 | -4.07 | -2.23 | 26 | 5.7 |
| HNRH1_HUMAN | 5031753 | 1.03 | 2.22 | 1.82 | 52 | 4.8 |
| 1433B_HUMAN | 4507949 | 3.02 | 2.11 | 2.42 | 28 | 4.7 |
| PRDX2_HUMAN | 32189392 | -3.59 | -1.69 | -2.32 | 23 | 5.5 |
| PHB_HUMAN | 4505773 | -14.89 | -0.98 | -5.62 | 28 | 5.6 |
| CBS_HUMAN | 4557415 | -1.27 | -2.80 | -2.29 | 59 | 6.3 |
| PEX19_HUMAN | 4506339 | 0.79 | 2.51 | 1.94 | 36 | 4.2 |
| LPPRC_HUMAN | 31621305 | 1.99 | 1.37 | 1.57 | 130 | 5.6 |
| CAZA2_HUMAN | 433308 | -1.98 | -2.05 | -2.03 | 35 | 5.6 |
| ST1A1_HUMAN | 847763 | -1.12 | -2.16 | -1.81 | 30 | 5.9 |
| SSRD_HUMAN | 5454090 | 2.26 | 6.74 | 5.25 | 18 | 5.6 |
| GDIR_HUMAN | 2624719 | -1.49 | -2.08 | -1.88 | 26 | 5.0 |
| 1433Z_HUMAN | 4507953 | 2.93 | 1.78 | 2.17 | 28 | 4.6 |

TABLE 7

| Uniprot ID | NCBI GI | E1 | E2 | 평균 | Mw | pI |
|---|---|---|---|---|---|---|
| SKP1_HUMAN | 25777713 | 2.41 | 1.07 | 1.52 | 19 | 4.2 |
| TCPB_HUMAN | 48146259 | 1.68 | 1.54 | 1.59 | 51 | 6.0 |
| SET_HUMAN | 145843637 | 5.59 | 1.63 | 2.95 | 20 | 4.8 |
| BDH_HUMAN | 17738292 | -0.07 | -2.38 | -1.61 | 29 | 8.1 |
| ST2A1_HUMAN | 29540545 | -4.66 | -2.90 | -3.48 | 33 | 5.4 |
| C1QBP_HUMAN | 1096067 | 0.50 | 2.03 | 1.52 | 32 | 4.3 |
| FCL_HUMAN | 4507709 | 1.64 | 1.99 | 1.87 | 42 | 6.2 |
| DPYS_HUMAN | 4503375 | 0.04 | -3.04 | -2.01 | 55 | 6.8 |
| UGPA_HUMAN | 2136353 | -2.45 | -2.34 | -2.38 | 55 | 7.4 |
| GLE1_HUMAN | 4557627 | 1.46 | 3.79 | 3.01 | 18 | 5.1 |
| TOIP1_HUMAN | 119611474 | -1.61 | -3.38 | -2.79 | 63 | 6.0 |
| DCXR_HUMAN | 7705925 | -1.51 | -1.75 | -1.67 | 25 | 10.1 |
| CS010_HUMAN | 3355455 | -0.65 | -2.30 | -1.75 | 14 | 6.3 |
| FAH2A_HUMAN | 4929679 | -1.24 | -2.75 | -2.25 | 33 | 6.6 |
| DBLOH_HUMAN | 13325198 | 3.77 | 0.89 | 1.85 | 19 | 4.8 |
| PCYOX_HUMAN | 6561481 | -3.43 | -0.58 | -1.53 | 59 | 6.6 |

The proteins listed in table 2 through table 7 show specific overexpression and underexpression in E1 and E2 HCC tissues compared to normal liver tissues and thus they can be used as proteomic marker for early detection of liver cancer. Further, the proteins listed above show distinguishable change of expression in the early stage of hepatocellular carcinoma potentially related to hepatocarcinogenesis, and therefore, could be used as a therapeutic targets for developing liver cancer drugs.

Effects

The present invention provides proteomic markers for early detection of liver cancer, compositions for diagnosing liver cancer that include materials that specifically detect changes of these proteomic markers, diagnostic kits for liver cancer that include above compositions, methods for diagnosis of liver cancer that use above protein markers, methods for screening therapeutic drugs for liver cancer using these markers, and the antibodies that specifically detects the above protein markers.

The above proteomic markers are specific for early-stage HCC and can be used for early diagnosis of liver cancer. Further, the physiological functions of these protein markers could be directly related to hepatocarcinogenesis such that these proteins can be used for in-depth study of mechanisms of hepatocarcinogenesis and as targets for therapeutic drugs of liver cancer.

Because of their specificity to early-stage HCC, the above proteomic markers are more clinically applicable and suitable as target proteins for therapeutic drugs of liver cancer compared to existing liver cancer markers detected only at the DNA or mRNA levels.

BRIEF DESCRIPTION OF THE DRAWINGS

FIG. 1. 2D Gel images (pI 3-11 NL) of Edmondson grade I hepatocellular carcinoma tissues (n=2), Edmondson grade II hepatocellular carcinoma tissues (n=4), and surrounding noncancerous tissues (n=5).

FIG. 2. 2D Gel images (pI 3-5.6 NL) of Edmondson grade I hepatocellular carcinoma tissues (n=2), Edmondson grade II hepatocellular carcinoma tissues (n=4), and surrounding noncancerous tissues (n=5).

FIG. 3. 2D Gel images (pI 5.3-6.5 L) of Edmondson grade I hepatocellular carcinoma tissues (n=2), Edmondson grade II hepatocellular carcinoma tissues (n=4), and surrounding noncancerous tissues (n=5).

FIG. 4. 2D Gel images (pI 6.2-7.5 L) of Edmondson grade I hepatocellular carcinoma tissues (n=2), Edmondson grade II hepatocellular carcinoma tissues (n=4), and surrounding noncancerous tissues (n=5).

The invention claimed is:

1. An isolated composition for early diagnosis of liver cancer comprising materials that can detect the presence, and expression levels, expression patterns or both of proteomic markers APOA1 isoform CRA b (apolipoprotein A-I, isoform CRA_b; NCBI GI:119587681); AKR1C4_HUMAN (Aldo-keto reductase family 1 member C4 (Chlordecone reductase) (CDR); NCBI GI:1705823); VCL_HUMAN (vinculin; NCBI GI:4507877); GLE1_HUMAN (GLE1 RNA export mediator homolog isoform 2; NCBI GI:4557627); and TOR1A1 P1_HUMAN (torsin A interacting protein 1, isoform CRA_b; NCBI GI:119611474) wherein the materials are a population of isolated antibodies that can specifically detect proteomic markers for early detection of liver cancer.

2. A population of isolated antibodies specific for proteomic markers APOA1 isoform CRA b (apolipoprotein A-I, isoform CRA_b; NCBI GI:119587681); AKR1C4_HUMAN (Aldo-keto reductase family 1 member C4 (Chlordecone reductase) (CDR); NCBI GI:1705823); VCL_HUMAN (vinculin; NCBI GI:4507877); GLE1_HUMAN (GLE1 RNA export mediator homolog isoform 2; NCBI GI:4557627); and TOR1A1 P1_HUMAN (torsin A interacting protein 1, isoform CRA_b; NCBI GI:119611474) for early detection of liver cancer.

* * * * *